United States Patent
Hasegawa (10) Patent No.: US 9,763,834 B2
(45) Date of Patent: Sep. 19, 2017

(54) ULTRASONIC OSCILLATION-INDUCED SERICIN EXTRACTION METHOD AND PROCESS FOR COATING SERICIN IN A GLOVE

(71) Applicant: Best-Kobo, Co. Ltd., Fukui (JP)

(72) Inventor: Tsukasa Hasegawa, Fukui (JP)

(73) Assignee: Best-Kobo, Co, LTD., Fukui (JP)

( * ) Notice: Subject to any disclaimer, the term of this patent is extended or adjusted under 35 U.S.C. 154(b) by 376 days.

(21) Appl. No.: 14/517,898

(22) Filed: Oct. 19, 2014

(65) Prior Publication Data
US 2015/0033442 A1   Feb. 5, 2015

Related U.S. Application Data

(63) Continuation-in-part of application No. PCT/JP2012/076605, filed on Oct. 15, 2012.

(51) Int. Cl.
  *A41D 19/02*  (2006.01)
  *A61F 13/10*  (2006.01)
  *D06M 15/15*  (2006.01)
  *A41D 19/00*  (2006.01)
  *A41D 19/04*  (2006.01)

(52) U.S. Cl.
  CPC ........ *A61F 13/104* (2013.01); *A41D 19/0055* (2013.01); *A41D 19/02* (2013.01); *A41D 19/04* (2013.01); *D06M 15/15* (2013.01)

(58) Field of Classification Search
  CPC ........ A61B 19/04; A61B 35/00; A41D 19/02; B82Y 30/00; C04B 41/009
  USPC ....... 2/167, 168, 169, 161.7; 427/180, 372.2
  See application file for complete search history.

(56) References Cited

U.S. PATENT DOCUMENTS

| | | | | |
|---|---|---|---|---|
| 2,273,995 A | * | 2/1942 | Rogerson | B29D 99/0067 2/167 |
| 4,466,151 A | * | 8/1984 | Barch | B05C 17/0207 15/227 |
| 5,581,812 A | * | 12/1996 | Krocheski | A41D 19/0006 2/161.6 |
| 6,117,119 A | * | 9/2000 | Gould | A61M 35/00 604/289 |
| 6,953,582 B2 | | 10/2005 | Chou | |

(Continued)

*Primary Examiner* — Tejash Patel
(74) *Attorney, Agent, or Firm* — Invent Capture, LLC.; Samuel S. Cho (57) ABSTRACT

A novel ultrasonic oscillation-induced sericin extraction method produces a high-molecular-weight sericin solution from silk cocoon threads at room temperature. In one embodiment, unique pH variation-resistant alkaline ionic water is produced from a novel strongly-alkaline ionic water generator device, wherein the unique pH variation-resistant alkaline ionic water is subsequently utilized as a beneficial solvent that contributes to the feasibility of the novel ultrasonic oscillation-induced sericin extraction method at room temperature. The high-molecular-weight sericin solution produced and coated in a glove provides a high coating adhesion for economical manufacturing of sericin-coated gloves, while also providing superb skin moisturizing and protection properties. Furthermore, once coated in a glove, the high molecular weight of sericin beneficially resists a rapid skin seepage of sericin to human skin layers, thereby acting as natural moisturizing factor (NMF) simulants on top of the human skin layers when the glove is worn.

14 Claims, 6 Drawing Sheets

Molecular Weight Comparison Between Applicant's High-Molecular Weight Sericin and Conventional Sericin (56) References Cited

U.S. PATENT DOCUMENTS

| | | | |
|---|---|---|---|
| 7,691,436 B2* | 4/2010 | Neuser | A41D 19/0058 427/181 |
| 7,750,073 B2* | 7/2010 | Brahms | A61K 8/31 424/401 |
| 8,458,818 B2 | 6/2013 | Neuser et al. | |
| 8,835,014 B2* | 9/2014 | Wang | A41D 19/0055 424/78.02 |
| 2003/0167555 A1* | 9/2003 | Han | A41D 19/001 2/161.6 |

* cited by examiner

An Ultrasonic Oscillation-Induced Sericin Extractor Apparatus

A Structural Snapshot of Silk

FIG. 2

COMPOSITION OF AMINO ACID OF SILK SERICIN*

| Amino acid | Molar percent |
|---|---|
| Asp | 18.71 |
| Ser | 32.16 |
| Glu | 3.83 |
| Gly | 16.43 |
| His | 1.46 |
| Arg | 3.74 |
| Thr | 8.04 |
| Ala | 4.35 |
| Pro | 0.97 |
| Cys | 0.13 |
| Tyr | 3.14 |
| Val | 2.56 |
| Met | 0.64 |
| Lys | 1.79 |
| Ile | 0.66 |
| Leu | 0.80 |
| Phe | 0.64 |

* Values are means by duplicate analysis.

300

Amino Acid Compositions in Silk Sericin

FIG. 3

A Comparison Between Eccrine Sweat and Applicant's High-Molecular Weight Sericin

Molecular Weight Comparison Between Applicant's High-Molecular Weight Sericin and Conventional Sericin

FIG. 6

ULTRASONIC OSCILLATION-INDUCED SERICIN EXTRACTION METHOD AND PROCESS FOR COATING SERICIN IN A GLOVE

BACKGROUND OF THE INVENTION

The present invention generally relates to sericin extraction and coating sericin on an object. More specifically, the present invention relates to separating and extracting sericin from silk by utilizing a novel method and a process. Furthermore, the present invention also relates to extracting and creating a sericin solution with a high molecular weight. In addition, the present invention also relates to coating a glove with the sericin solution.

Sericin is a protein created by *Bombyx mori*, or silkworms, which produce silk. The silk produced by the silkworms include fibroin, which is structurally located in the center of the silk, and sericin, which surrounds the fibroin as gummy substances. For thousands of years, humans have utilized sericin from silk for cosmetic and skin treatment purposes, as many people since the antiquities believed that silk sericin exhibits anti-aging, moisturizing, and protective effects on human skin and hair.

Modern scientific studies also have confirmed numerous dermatological benefits of applying sericin on a skin layer. Sericin's chemical composition is found to include many amino acids, which closely resemble natural moisturizing factor (NMF) in human eccrine sweat. When coated on top of a skin layer, sericin has shown superior moisture retention and substantially less skin irritation, compared to conventional oil-based and water-based moisturizing lotions. Furthermore, in some studies, skin layers that were coated with sericin have also exhibited substantially better ultraviolet (UV) ray blocking, anti-aging, anti-microbial, and wound-healing tendencies, compared to the control groups of skin layers that did not have sericin coats.

Typically, silk threads, which are mostly made of fibroin in the natural bulk silk material, garner substantially more premium over sericin in the commodities market. Therefore, the conventional method of sericin extraction has been fundamentally optimized for efficient and effective extraction and processing of the silk threads, rather than the extraction of sericin. From silk processing perspective, sericin has been often viewed merely as a secondarily-lucrative byproduct from the silk thread extraction and processing operation.

Unfortunately, the conventional method of sericin extraction from a natural bulk silk material involves heating up the natural bulk silk material in order to extract and separate the silk threads from sericin. In a conventional high-temperature separation and extraction process, the extracted sericin solution exhibits a low molecular weight due to evaporation of moisture and particles. Scientific studies have shown that low-molecular-weight sericin tend to seep into the skin too soon and too easily, instead of forming a protective moisturizing barrier on top of the human skin as a close simulant to natural moisturizing factor (NMF) on a stratum corneum (SC) layer of the human skin. Many scientific studies have also shown that NMF's hygroscopic and water-soluble compounds in the SC layer of the human skin provide a natural moisturizing balance to the human skin. Furthermore, some scientists also believe that a skin moisturizing solution that chemically resembles the human skin's natural moisturizing factor (NMF), which forms a protective barrier on top of the human skin, may act as ideal skin humectants.

Because sericin is a close chemical simulant to the NMF, it may be advantageous to devise a novel sericin extraction method that retains a high molecular weight of the sericin from the natural bulk silk material, when the sericin is separated from the natural bulk silk material. Furthermore, it may also be advantageous to coat a glove with the high-molecular-weight sericin produced from the novel sericin extraction method, so that the high-molecular-weight sericin provides a protective natural moisturizing factor (NMF) simulant to a wearer's hand for moisturizing and retaining natural humectants on the wearer's hand. In addition, it may also be advantageous to devise a glove that exhibits anti-microbial, anti-aging, and wound-healing benefits to the wearer's hand, while providing a simulated NMF barrier to the wearer's hand for natural hand moisture retention.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In one embodiment of the invention, a method for producing a sericin-coated glove is disclosed. This method comprises the steps of: generating pH variation-resistant alkaline ionic water from a strongly-alkaline ionic water generator device; immersing silk cocoon threads in the pH variation-resistant alkaline ionic water; oscillating the silk cocoon threads immersed in the pH variation-resistant alkaline ionic water with ultrasonic waves at room temperature, which separates the silk cocoon threads into a high-molecular-weight sericin solution and fibroin; and spraying the high-molecular-weight sericin solution into an inner surface of a glove, or immersing the glove into the high-molecular-weight sericin solution to produce the sericin-coated glove, wherein the high-molecular-weight sericin solution naturally and adheres to the inner surface of the glove without an external adhesive agent.

In another embodiment of the invention, a sericin-coated glove is disclosed. This glove comprises: a glove made of rubber or another resin material; and a sericin solution sprayed into or coated to an inner surface of the glove.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble apparatuses and methods for ultrasonic oscillation-induced sericin extraction and processing. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention do not inherently indicate any particular order nor imply any limitations in the invention.

For the purpose of describing the invention, a term "sericin" is defined as a protein created by *Bombyx mori*, or other creatures that produce silk, which produce silk. The silk produced by *Bombyx mori* or other creatures include fibroin, which is structurally located in the center of the silk, and sericin, which surrounds the fibroin as gummy substances.

In addition, for the purpose of describing the invention, a term "natural moisturizing factor," or NMF, is defined as naturally-occurring substances in human eccrine sweat, breakdown substances from topmost skin layers, lipids, and/or a chemical simulant (i.e. a chemically-similar substance) to the naturally-occurring substances in human eccrine sweat.

Furthermore, for the purpose of describing the invention, a term "high-molecular-weight sericin" is defined as a sericin solution with sufficient average molecular weight to stay above a human skin layer for forming a moisturizing and protective NMF simulant layer. In one example, a sericin solution with an average molecular weight of 30,000 g/mol or higher may be considered the "high-molecular-weight sericin" that meets this requirement. In another example, a sericin solution with an average molecular weight range of 37,000 g/mol~97,000 g/mol may be considered an ideal range for the "high-molecular-weight sericin." Yet in another example, because a conventional thermal method of sericin extraction struggles to provide an average sericin molecular weight above 67,000 g/mol, the "high-molecular-weight sericin" refers to a sericin solution with an average molecular weight above 67,000 g/mol.

In addition, for the purpose of describing the invention, a term "low-molecular-weight sericin" is defined as a sericin solution that has a lower average molecular weight than the "high-molecular-weight sericin," as defined in the Specification.

One aspect of an embodiment of the present invention is providing a novel sericin extraction method that retains a high molecular weight of the sericin from the natural bulk silk material, when the sericin is separated from the natural bulk silk material.

Another aspect of an embodiment of the present invention is providing a glove coated with the high-molecular-weight sericin produced from the novel sericin extraction method. Preferably, the high-molecular-weight sericin provides a protective natural moisturizing factor (NMF) simulant to a wearer's hand for moisturizing and retaining natural humectants on the wearer's hand.

Yet another aspect of an embodiment of the present invention is providing a sericin-coated glove that exhibits anti-microbial, anti-aging, and wound-healing benefits to the wearer's hand, while providing a simulated NMF barrier to the wearer's hand for natural hand moisture retention.

Conventional methods of extracting sericin involve thermal treatment of the natural bulk silk material, which results in a low molecular weight for the extracted sericin solution. A low-molecular-weight sericin solution is generally undesirable for human skin moisturizer and protection applications, because the low molecular weight of sericin can cause a rapid skin seepage of sericin that reduces the effectiveness of sericin as human skin moisturizer and protectant.

Furthermore, the extracted sericin solution with a low molecular weight may require a separate adhesive or fixing agent, because the inherent adhesion of the low-molecular-weight sericin is insufficient for direct coating to an object. Therefore, with conventional sericin extraction methods, application of sericin to an inner surface of a glove was both difficult and impractical.

Figure 1:
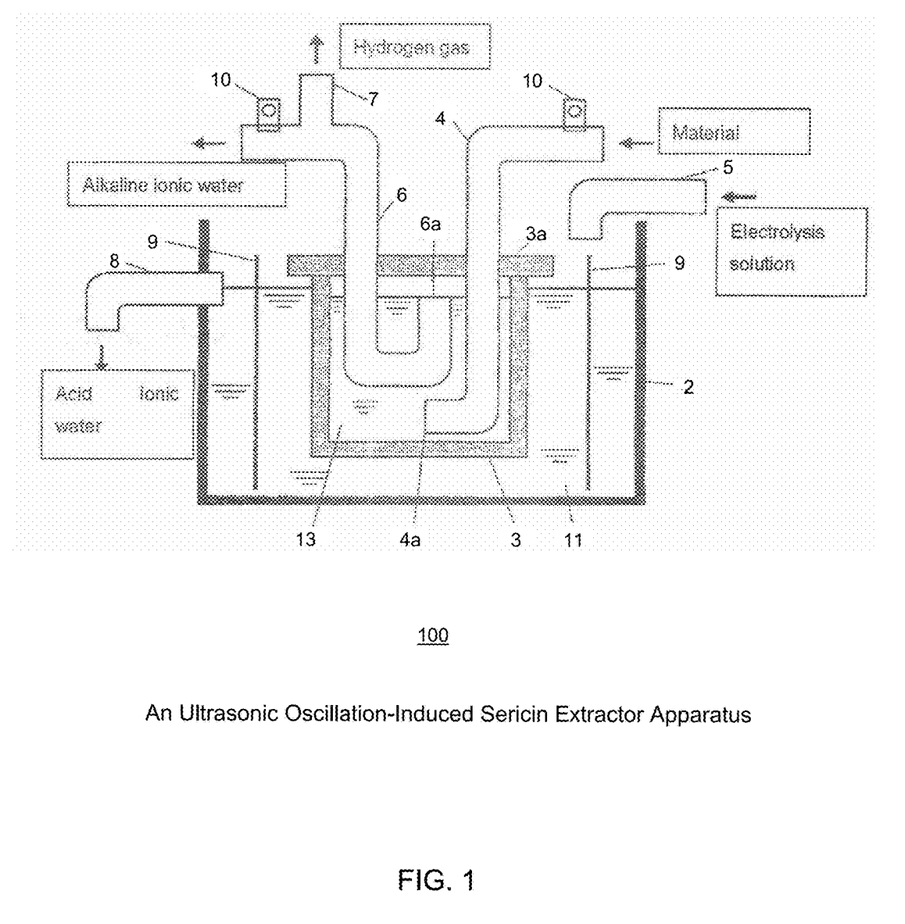
FIG. 1 shows an example of a strongly-alkaline ionic water generator device that produces non-degrading and low pH-variation strong alkaline ionic water, which is used as a solvent in ultrasonic oscillation-induced sericin extraction, in accordance with an embodiment of the invention.

FIG. 1 shows an example of a strongly-alkaline ionic water generator device (100) that produces non-degrading and low pH-variation strong alkaline ionic water, which is used as a solvent in ultrasonic oscillation-induced sericin extraction, in accordance with an embodiment of the invention. In a preferred embodiment of the invention, the strongly-alkaline ionic water generator device (100) generates a special type of non-degrading and low pH-variation strong alkaline ionic water that enables extraction of sericin at room temperature (e.g. 20~26 degrees Celsius, or another ordinary room temperature range) by immersing cocoon threads in this special type of strongly-alkaline ionic water and subjecting the cocoon threads in ultrasonic oscillation.

In the preferred embodiment of the invention, the strongly-alkaline ionic water generator device (100) comprises a recipient container (2), a barrier membrane (3), a first pipe fitting (4) to supply waster as material, a feed opening (4a) of the first pipe fitting, a refill tube (5) for electrolysis solution, a second pipe fitting (6) to collect alkaline ionic water, an intake (6a) of the second pipe fitting, an outlet tube (7) for hydrogen gas, an outlet tube (8) for acid ionic water, one or more positive electrodes (9), one or more negative electrodes (10), an anode chamber (11) that serves as a formation field of acid ionic water, and a formation field (13) of alkaline ionic water contained by the barrier membrane (3).

Continuing with FIG. 1, in the preferred embodiment of the invention, strongly-alkaline ionic water desirable for extraction and processing of a high-molecular-weight sericin solution is produced by the strongly-alkaline ionic water generator device (100). The barrier membrane (3) of the strongly-alkaline ionic water generator device (100) separates the anode chamber (11) that serves as the formation field of acid ionic water from the formation field (13) of alkaline ionic water, which is contained by the barrier membrane (3). The second pipe fitting (6) to collect alkaline ionic water is also utilized as the negative electrode (10).

As shown in FIG. 1, the strongly-alkaline ionic water generator device (100) has incorporates the recipient container (2), the barrier membrane (3), the first pipe fitting (4) to supply waster as material, the refill tube (5) for electrolysis solution, and the second pipe fitting (6) to collect the alkaline ionic water. The strongly-alkaline ionic water generator device (100) also includes the outlet tube (7) of hydrogen bifurcated from the second pipe fitting (6) that collects the alkaline ionic water, and the outlet tube (8) for collecting the acid ionic water. Furthermore, in the preferred embodiment of the invention, one or more positive electrodes (9) are installed inside the recipient container (2) for electrolysis.

In the preferred embodiment of the invention, the recipient container (2) has an opening on its top surface and includes the barrier membrane (3), which may be tub-shaped. Preferably, the barrier membrane (3) is made of terracotta or another ceramic material, and is capable of containing some fluid inside. In the interior of this barrier membrane (3), material water is supplied via the first pipe fitting (4) with the feed opening (4a) that reaches near the bottom surface of the barrier membrane (3). The other end of the first pipe fitting (4) is connected to the supply source of material water (i.e. labeled in FIG. 1 as "material") that may be connected to additional plumbing. Furthermore, the top portion (3a) of the barrier membrane (3) can also be terracotta, another ceramic material, or another substance appropriate for containing some fluid inside.

Continuing with FIG. 1, the second pipe fitting (6) to collect alkaline ionic water has the intake (6a) on one end, which is oriented upward in the barrier membrane (3), and can also be folded upward in a position closer to the other end to be derived to the upward direction of the barrier membrane (3). The outlet tube (7) of hydrogen gas is bifurcated upwards in the upper part of the barrier membrane (3). In the preferred embodiment of the invention, the first pipe fitting (4) and the second pipe fitting (6) each incorporate one or more negative electrodes (10) and are made of electrically-conductive materials that are preferably resistant to corrosion.

Furthermore, the interior of the recipient container (2), which is the exterior of the barrier membrane (3), functions as the anode chamber (11) that accommodates formation of acid ionic water during electrolysis. As shown in FIG. 1, one or more positive electrodes (9) are installed in the anode chamber (11), and the electrolysis solution is supplied via the refill tube (5) for the electrolysis solution. Each of the positive electrodes (9) may be a plate or a rod-shaped electrode. Because a plate potential (i.e. the positive electrodes (9)) is installed in the anode chamber (11) and a cathode potential, which is a negative electric potential to the plate potential, is installed in the interior of the barrier membrane (3), the interior of the barrier membrane (3) becomes the formation field of alkaline ionic water, and the anode chamber (11) becomes the formation field of acid ionic water.

Subsequently, the material water supplied to the interior of the barrier membrane (3) is decomposed by electric current, and alkaline ionic water is formed in the formation field (13) of alkaline ionic water while the anode chamber (11) becomes the formation field of acid ionic water. The acid ionic water in the anode chamber (11) is discharged to the exterior of the recipient container (2) through the outlet tube (8) at a specific height of water surface, wherein the specific height is the distance between the outlet tube (8) and the bottom surface of the recipient container (2) in case of the preferred embodiment of the invention, as shown in FIG. 1. Furthermore, in the preferred embodiment of the invention, the intake (6a) of the second pipe fitting (6) collects the alkaline ionic water formed inside of the barrier membrane (3), and transmits the alkaline ionic water to an external reservoir located on the other end of the second pipe fitting (6), while the hydrogen gas is separated by the outlet tube (7) in mid-course.

Compared to conventional electrolysis processing methods for extracting alkaline ionic water, the alkaline ionic water produced by the strongly-alkaline ionic water generator device (100) in accordance with an embodiment of the invention has uniquely desirable characteristics for sericin extraction, such as less or minimal pH variations relative to elapsed time, physical agitation, and physical oscillation of the alkaline ionic water. These desirable traits make the uniquely-produced and pH variation-resistant alkaline ionic water a novel and desirable solvent for the ultrasonic oscillation of the cocoon threads for extraction of sericin at room temperature.

In one embodiment of the invention, the cocoon threads can be immersed in the uniquely-produced and pH variation-resistant alkaline ionic water from the strongly-alkaline ionic water generator device (100), and then are subjected to physical oscillation with ultrasonic wave and/or with magnetic field at room temperature. The novel ultrasonic-induced physical oscillation of the cocoon threads immersed in the uniquely-produced and pH variation-resistant alkaline ionic water results in separation and extraction of the high-molecular-weight sericin solution from the cocoon threads. The extraction of sericin at room temperature using the ultrasonic oscillation of the cocoon threads avoids the conventional thermal treatment of the cocoon threads, thereby resulting in the high molecular weight of the sericin solution, which is particularly desirable for human skin moisturization and protection applications. The high-molecular-weight sericin solution produced in accordance with an embodiment of the invention also provides better adhesion to an object, thereby enabling sericin coating on a glove to be a more economical and commercially-streamlined process than a conventional process requiring additional adhesive materials for sericin coating.

Continuing with FIG. 1, in one embodiment of the invention, a glove can first be manufactured primarily with nitryl (i.e. a synthetic resin material). Then, the interior of the glove is uniformly sprayed with the high-molecular-weight sericin solution prepared by the novel ultrasonic-induced sericin extraction process with the uniquely-produced and pH variation-resistant alkaline ionic water from the strongly-alkaline ionic water generator device (100). Preferably, the average molecular weight of the high-molecular-weight sericin solution is more than 60,000 g/mol. However, in some instances, the average molecular weight above 30,000 g/mol may be acceptable for sericin coating applications. Then, the glove can be dried naturally or artificially with an accelerated drying process, which adheres and cures the high molecular sericin solution to the interior surface of the glove.

In one experimental example of the sericin coating process in accordance with an embodiment of the invention, protein and amino acids of the sericin solution coated on a glove was measured and observed on the surface of the glove as a bluish-purple color reaction. The bluish-purple color reaction suggested that the sericin solution produced and coated to the glove, in accordance with an embodiment of the invention, was firmly adhered to the glove despite the low concentration of sericin (i.e. approximately 0.1~0.2 percent) in this particular experimental example. The high level of adhesion of the sericin solution, even in the low concentration of sericin, can be attributed to the high molecular weight of the sericin solution, which is made possible by the novel ultrasonic-induced sericin extraction process with the uniquely-produced and pH variation-resistant alkaline ionic water as the solvent from the strongly-alkaline ionic water generator device (100).

Figure 2:
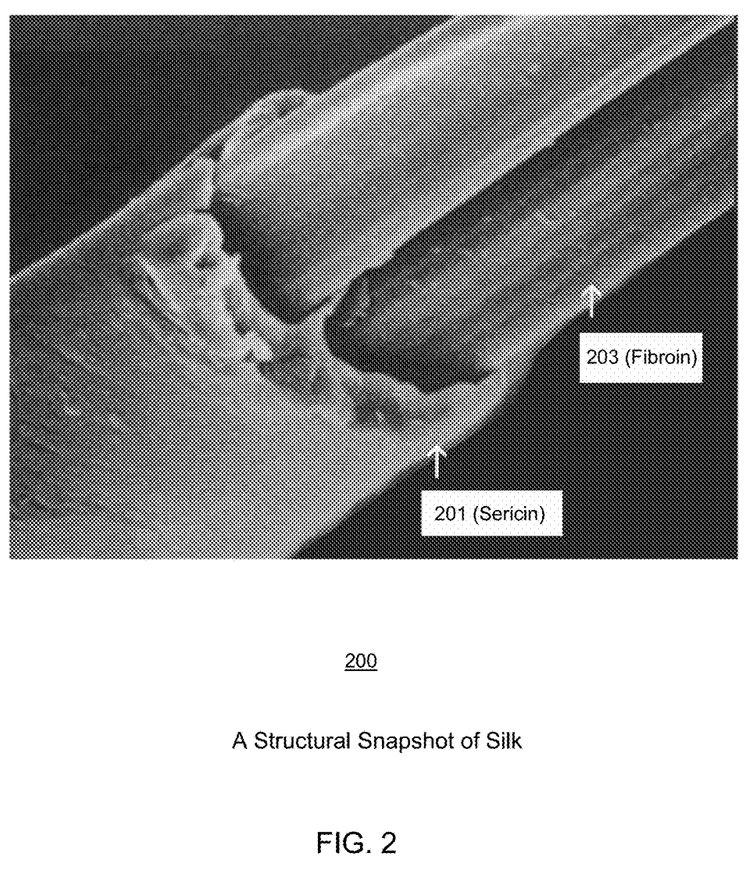
FIG. 2 shows a structural snapshot of silk.

FIG. 2 shows a structural snapshot (200) of a silk cocoon thread. The silk cocoon thread comprises fibroin (203), which is structurally located in the center of the silk cocoon thread, and sericin (201), which surrounds the fibroin as gummy substances. The fibroin (203) is typically extracted for production of silk threads, which are used for clothes, carpets, and other textile manufacturing. The sericin (201), on the other hand, is extracted for cosmetic purposes and skin moisturization, protection, and treatment. In context of one or more embodiments of the invention, a high-molecular-weight sericin solution is produced by a novel ultrasonic oscillation-induced sericin extraction process at room temperature while utilizing unique pH variation-resistant alkaline ionic water as the solvent for immersing the silk cocoon threads. The unique pH variation-resistant alkaline ionic water is first produced from a novel strongly-alkaline ionic water generator device (e.g. 100 of FIG. 1), wherein the unique pH variation-resistant alkaline ionic water is subsequently utilized as a beneficial solvent that contributes to the feasibility of the novel ultrasonic oscillation-induced sericin extraction method at room temperature.

Then, the high-molecular-weight sericin solution extracted from the novel production methods and processes of the present invention is sprayed in the interior surface of a glove to produce a sericin-coated glove. The high molecular weight of sericin provides a high coating adhesion for economical manufacturing of sericin-coated gloves, while also providing superb skin moisturizing and protection properties. Furthermore, once coated in a glove, the high molecular weight of sericin beneficially resists a rapid skin seepage of sericin to human skin layers, thereby acting as natural moisturizing factor (NMF) simulants as a semi-occlusive layer on top of the human skin layers when the glove is worn by a user.

Sericin-coated gloves may be particularly useful to medical professionals, such as doctors, nurses, and any other personnel, who are routinely required to wear medical exam gloves for patient inspection, surgery, and treatment. Even though some conventional medical gloves are coated with aloe vera or other skin-moisturizing materials to reduce dryness of hand due to repeated cleansing and medical glove wearing, medical gloves in the market today are yet to be coated with sericin, which is compositionally a closer chemical simulant to human skin's natural moisturizing factors (NMF's). Moreover, sericin-coated gloves may also be beneficial for hand wound healing, hand moisturization, and anti-aging hand treatments for patients and beauty-conscious users. Various embodiments of the present invention improve the adhesion of sericin to gloves by increasing the molecular weight of sericin solution, while also improving the skin moisturizing and protection quality of sericin by increasing the average molecular weight of the sericin coats, which minimizes early skin seepage of the sericin coats in human skin layers.

Figure 3:
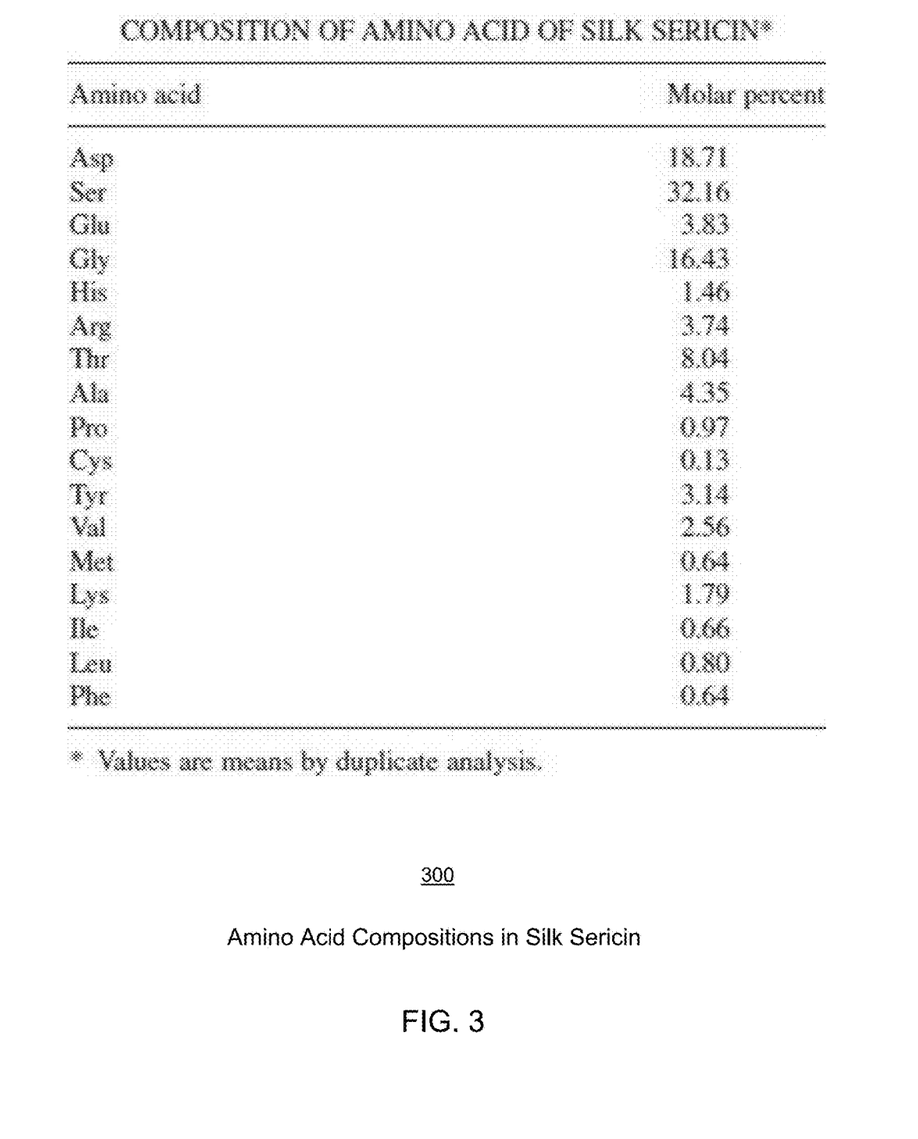
FIG. 3 shows amino acid compositions in silk sericin.

FIG. 3 shows a table (300) indicating amino acid compositions in silk sericin. Silk sericin includes a variety of amino acids that resemble compositions of naturally-occurring human eccrine sweat, such as aspartic acid (Asp), serine (Ser), glycine (Gly), alanine (Ala), threonine (Thr), glutamic acid (Glu), histidine (His), arginine (Arg), valine (Val), proline (Pro), leucine (Leu), tyrosine (Tyr), lysine (Lys), isoleucine (Ile), phenylalanine (Phe), tryptophan, methionine (Met), and cystine (Cys). The molar percentages listed for each of these amino acids in the table (300) in FIG. 3 are averaged values from duplicated analysis in a sample of a sericin solution extracted from a bulk silk material. Because the amino acids present in silk sericin are very similar to the chemical compositions found in naturally-occurring human eccrine sweat, silk sericin is an excellent chemical simulant of natural moisturizing factors (NMF's) for optimal skin moisturization, treatment, and protection against dryness, wounds, and ultraviolet-related skin damages.

Figure 4:
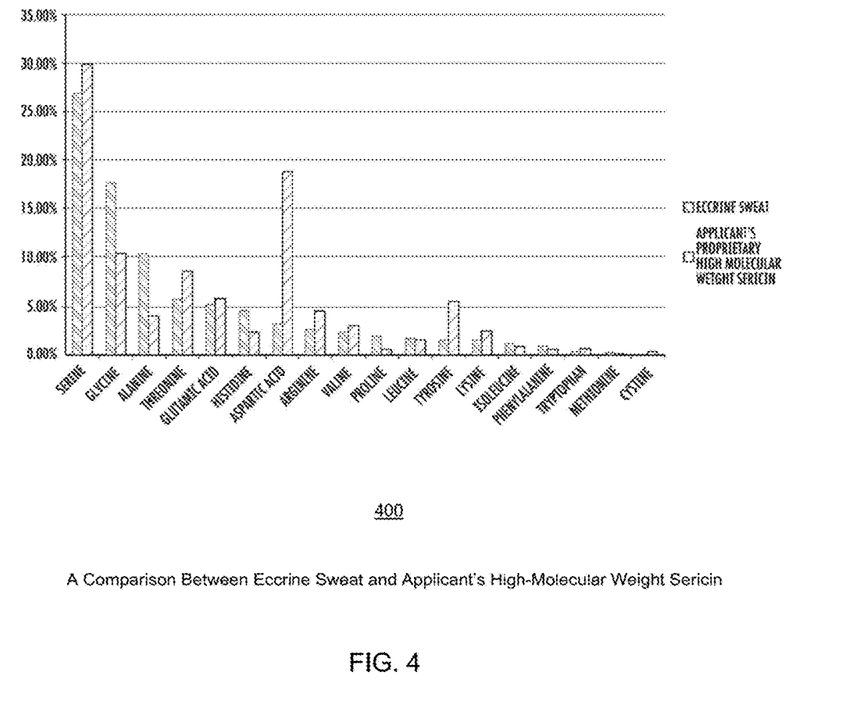
FIG. 4 shows a comparison between eccrine sweat and applicant's high-molecular weight sericin, in accordance with an embodiment of the invention.

FIG. 4 shows a comparison chart (400) between eccrine sweat and applicant's high-molecular weight sericin, in accordance with an embodiment of the invention. As indicated in this comparison chart (400), the high-molecular weight sericin produced by an embodiment of the present invention includes numerous amino acids that also occur naturally in human eccrine sweat. For example, amino acids such as serine (Ser), glycine (Gly), alanine (Ala), threonine (Thr), glutamic acid (Glu), histidine (His), and aspartic acid (Asp) are present in both the human eccrine sweat and the high-molecular weight sericin produced by an embodiment of the present invention.

The comparison chart (400) in FIG. 4 is an indication that the amino acids present in the high-molecular-weight sericin are very similar to the chemical compositions of the naturally-occurring human eccrine sweat. Because the high-molecular-weight sericin tends to resist a rapid skin seepage on top of human skin layers, in contrast to lower-molecular-weight sericin, the high-molecular-weight sericin acts as an excellent simulant of natural moisturizing factors (NMF's) for optimal skin moisturization, treatment, and protection against dryness, wounds, and ultraviolet-related skin damages.

Figure 5:
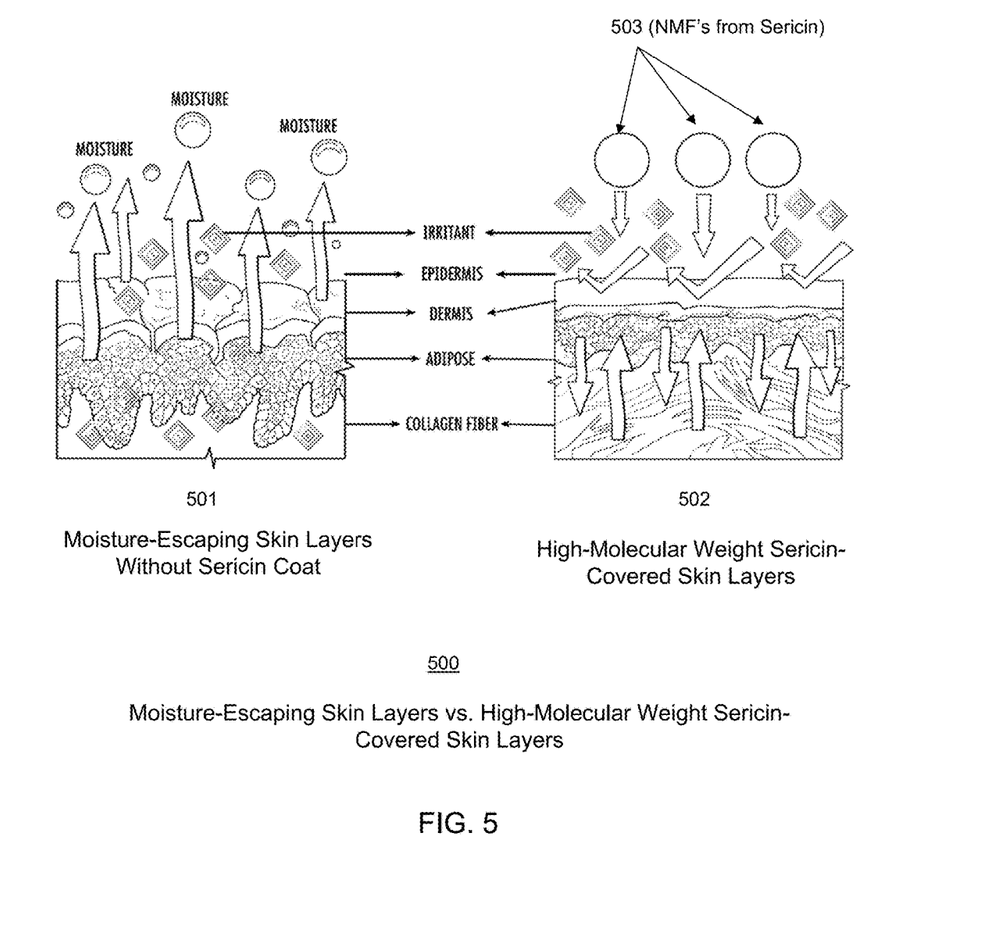
FIG. 5 shows a comparison between moisture-escaping skin layers and high-molecular weight sericin-covered skin layers, in accordance with an embodiment of the invention.

FIG. 5 shows a comparison between moisture-escaping skin layers in a left-side diagram (501) and high-molecular-weight sericin-covered skin layers in a right-side diagram (502), in accordance with an embodiment of the invention. In the left-side diagram (501), human skin layers are exposed to external elements without humectants or moisturizing layers. Therefore, any external irritants and ultraviolet rays can harm, inflame, and/or dry out the epidermis and sometimes even deeper layers (i.e. dermis, adipose, collagen fiber) of the human skin. As shown in the left-side diagram (501), moisture can easily escape the human skin layers when there is no humectants or moisturizing layers on top of the epidermis. Even though human skin layers can generate natural moisturizing factor (NMF) as eccrine sweat, frequent washing and/or exposure to sun and other external elements reduce chances of NMF's from staying on top of the epidermis, and moistures can easily escape the human skin layers, which contribute to drying, aging, and damaging of the skin layers.

On the other hand, the right-side diagram (502) shows the high-molecular-weight sericin-covered skin layers. The high-molecular-weight sericin acts as NMF simulants (503), which effectively humidify, protect, and heal the epidermis and the underlying skin layers from drying, aging, and UV-related damages. Furthermore, the high molecular weight of the sericin prevents the NMF simulants (503) from rapidly seeping into the human skin layers. Unlike lower-molecular-weight sericin solutions, the high-molecular-weight sericin tends to form a lasting NMF simulant layer (503) on top of the epidermis layer, thereby maximizing effectiveness of skin humidifying and protective benefits from sericin.

In a preferred embodiment of the invention, the high-molecular-weight sericin may have an average molecular weight of 30,000 g/mol or higher. In another embodiment of the invention, the high-molecular-weight sericin may have an average molecular weight of 37,000 g/mol~97,000 g/mol. Yet in another embodiment of the invention, the high-molecular-weight sericin may have an average molecular weight above 67,000 g/mol for a maximum humidifying and protective benefit to the human skin.

Figure 6:
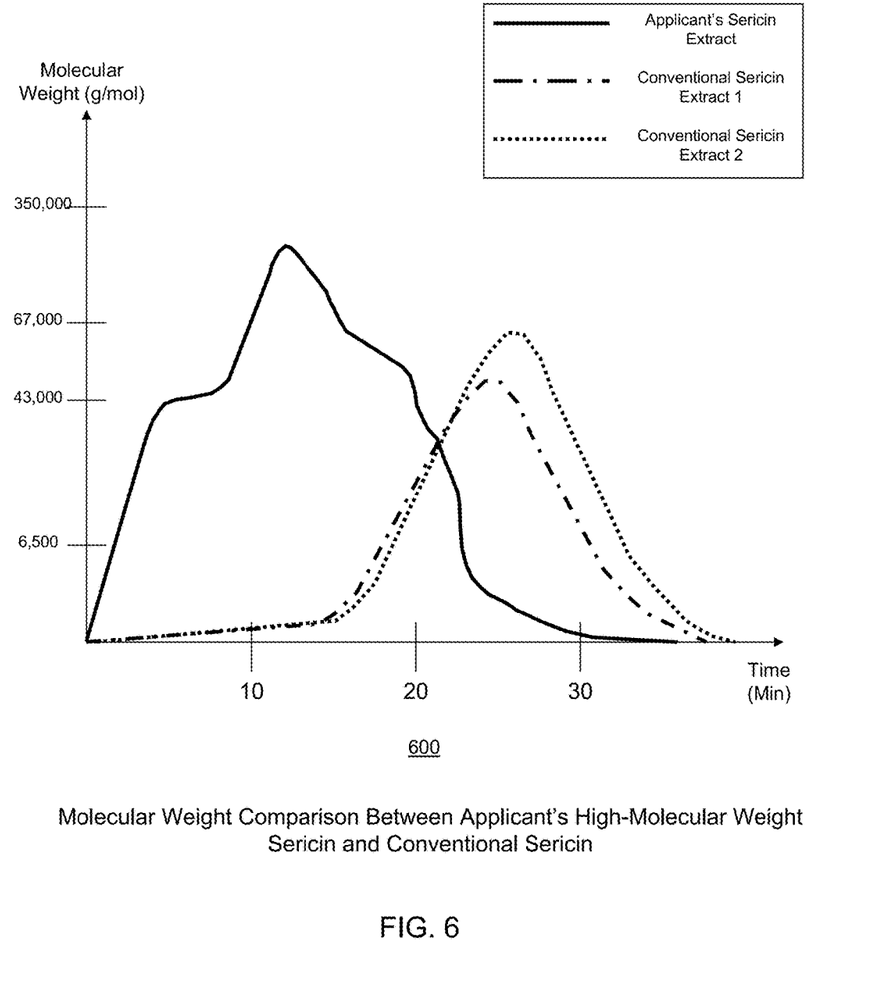
FIG. 6 shows a molecular weight comparison between applicant's high-molecular weight sericin and conventional sericin, in accordance with an embodiment of the invention.

FIG. 6 shows a molecular weight comparison chart (600) between applicant's high-molecular-weight sericin and conventional sericin solutions, in accordance with an embodiment of the invention. As shown in the molecular weight comparison chart (600), Applicant's sericin extract shows substantially higher molecular weight compared to conventional sericin extracts, which are shown in perforated lines. In some elapsed time segments, Applicant's sericin extract exhibits approximately ten times higher average molecular weight than the two conventional sericin extracts that were analyzed in this molecular weight comparison. Applicant's sericin extract is able to provide up to 350,000 g/mol in molecular weight in some elapsed time segments, as shown in the molecular weight comparison chart (600), with the ideal average molecular weight range of 37,000 g/mol~97,000 g/mol.

As described previously, unique pH variation-resistant alkaline ionic water produced from a novel strongly-alkaline ionic water generator device, in accordance with an embodiment of the invention, is utilized as a solvent for separating silk cocoon threads into a high-molecular-weight sericin solution and fibroin at room temperature, with ultrasonic physical oscillation of the silk cocoon threads immersed in the solvent. The high-molecular-weight sericin solution produced and coated in a glove provides a high coating adhesion for economical manufacturing of sericin-coated gloves, while also providing superb skin moisturizing and protection properties.

This particular molecular weight comparison chart (600) in FIG. 6 was obtained with Shimadzu's LC-9AD equipment with Pharmacia's Superdex 75 HR 10 mm×300 mm as the column, and 0.2 M NaCl 0.05 M Tris HCl Buffer as the eluent. Flow speed for the analysis of the molecular weight of the three sericin extracts was 0.7 ml/min, and the column temperature was 25 degree Celsius. Furthermore, an ultraviolet ray with the wavelength of 275 nm was utilized for the molecular weight analysis.

Various embodiments of the invention of have been described above and also illustrated in part by FIGS. 1~6. The present invention provides several advantages over conventional extraction and utilization of sericin. One advantage of an embodiment of the present invention is that a novel strongly-alkaline ionic water generator device provides unique pH variation-resistant alkaline ionic water, which in turn enables a novel room-temperature extraction of a high-molecular-weight sericin solution from silk cocoon threads, when the unique pH variation-resistant alkaline ionic water is utilized as a unique solvent during an ultrasonic oscillation of the silk cocoon threads immersed in the unique solvent.

Another advantage of an embodiment of the present invention is providing a glove coated with the high-molecular-weight sericin produced from the novel sericin extraction method, wherein the high-molecular-weight sericin provides a high inherent adhesion to the glove, while also acting as a superb natural moisturizing factor (NMF) simulant to a wearer's hand for moisturizing and retaining natural humectants on the wearer's hand.

Yet another advantage of an embodiment of the present invention is providing a sericin-coated glove that exhibits anti-microbial, anti-aging, and wound-healing benefits to the wearer's hand, while providing a simulated NMF barrier to the wearer's hand for natural hand moisture retention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for producing a sericin-coated glove, the method comprising the steps of:
   generating pH variation-resistant alkaline ionic water from an alkaline ionic water generator device;
   immersing silk cocoon threads in the pH variation-resistant alkaline ionic water;
   oscillating the silk cocoon threads immersed in the pH variation-resistant alkaline ionic water with ultrasonic waves at room temperature, which separates the silk cocoon threads into a high-molecular-weight sericin solution and fibroin; and
   spraying the high-molecular-weight sericin solution into an inner surface of a glove, or immersing the glove into the high-molecular-weight sericin solution to produce the sericin-coated glove, wherein the high-molecular-weight sericin solution naturally adheres to the inner surface of the glove without an external adhesive agent.

2. The method of claim 1, further comprising a step of drying the glove after the step of spraying the high-molecular-weight sericin solution into the inner surface of the glove.

3. The method of claim 1, wherein the high-molecular-weight sericin solution has an average molecular weight above 30,000 g/mol.

4. The method of claim 1, wherein the high-molecular-weight sericin solution has an average molecular weight between 37,000 g/mol and 97,000 g/mol.

5. The method of claim 1, wherein the high-molecular-weight sericin solution forms a natural moisturizing factor (NMF) simulant layer on top of an epidermis human skin layer without being rapidly seeped into the epidermis human skin layer, when the sericin-coated glove is worn.

6. The method of claim 1, wherein the room temperature is between 20 and 26 degrees Celsius.

7. The method of claim 1, wherein the pH variation-resistant alkaline ionic water resists changes in pH levels over time and over physical agitations and oscillations of the pH variation-resistant alkaline ionic water in the step of oscillating the silk cocoon threads with the ultrasonic waves at the room temperature.

8. The method of claim 1, wherein the glove is made of rubber or other resin materials prior to the step of spraying the high-molecular-weight sericin solution into the inner surface of the glove to produce the sericin-coated glove.

9. The method of claim 1, wherein the step of oscillating the silk cocoon threads immersed in the pH variation-resistant alkaline ionic water with the ultrasonic waves is performed by an ultrasound-emitting device with the pH variation-resistant alkaline ionic water as a solvent.

10. A sericin-coated glove comprising:
    a glove made of rubber or another resin material; and
    a sericin solution extracted from protein molecules originating from silkworm, wherein the sericin solution is sprayed into or coated to an inner surface of the glove.

11. The sericin-coated glove of claim 10, wherein the sericin solution naturally adheres to the inner surface of the glove without an external adhesive agent.

12. The sericin-coated glove of claim 10, wherein the sericin solution has an average molecular weight above 30,000 g/mol.

13. The sericin-coated glove of claim 10, wherein the sericin solution forms a natural moisturizing factor (NMF) simulant layer on top of an epidermis human skin layer without being rapidly seeped into the epidermis human skin layer, when the sericin-coated glove is worn.

14. The sericin-coated glove of claim 10, wherein the rubber is either natural or synthetic.

* * * * *